US005143825A

United States Patent [19]

Chacko et al.

[11] Patent Number: 5,143,825

[45] Date of Patent: Sep. 1, 1992

[54] STABILIZED SUBSTRATE FOR USE IN AN IMMUNOASSAY

[75] Inventors: Koshy T. Chacko, Mundelein; Karen L. Fitzgerald, Wheeling; James J. Markese, Downers Grove, all of Ill.

[73] Assignee: Abbott Laboratories, Abbott Park, Ill.

[21] Appl. No.: 487,331

[22] Filed: Mar. 1, 1990

[51] Int. Cl.[5] ........................ G01N 33/52; C12Q 1/42

[52] U.S. Cl. .................................... 435/7.9; 435/7.92; 435/21; 435/968; 435/963

[58] Field of Search ........................ 435/7.9, 7.72, 963, 435/967, 968, 21

[56] References Cited

U.S. PATENT DOCUMENTS 4,400,464 8/1983 Vormbrock et al. ................ 435/21

4,666,830 5/1987 Wagner ................................ 435/7.1

OTHER PUBLICATIONS

Grant & Hackh's Chemical Dictionary, Grant et al, Editors 5th Ed. 1987 p. 200.

*Primary Examiner*—Esther L. Kepplinger
*Assistant Examiner*—Carol E. Bidwell
*Attorney, Agent, or Firm*—Richard D. Schmidt

[57] ABSTRACT

A 4-methylumbelliferyl phosphate substrate for use in conducting an immunoassay is disclosed. The substrate contains 0.1 gram mole per liter 2-amino-2-methyl-1-propanol, 0.01 to 0.05 gram mole per liter EDTA, added as trisodium EDTA, 1 gram per liter sodium azide, 1.2 milligram mole per liter 4-methylumbelliferyl phosphate and 4 milligram moles per liter tetramisole. The pH of the substrate disclosed is 10.3.

5 Claims, No Drawings

STABILIZED SUBSTRATE FOR USE IN AN IMMUNOASSAY

FIELD OF THE INVENTION

This invention relates to a stabilized substrate for use in an immunoassay. The substrate comprises 4-methylumbelliferyl phosphate, and is stabilized with ethylene diamine tetraacetic acid ("EDTA") or with ethylene glycol-bis-(-aminoethyl)-N,N,N,N'-tetraacetic acid ("EGTA").

BACKGROUND OF THE INVENTION

The following discussion of immunoassays and definitions of terms often used with respect to immunoassays are set forth herein as background to facilitate the understanding of the disclosure and claims hereof.

The term "analyte" refers to the substance, such as IgE antibody, to be detected.

The term "test sample" typically refers to a sample of body fluid such as plasma, serum, ascites, lymphatic fluids, cerebral spinal fluid, nipple fluid discharge, urine and other body fluids that may contain the analyte of interest. Optionally, the test sample can be diluted in a suitable diluent buffer, such as phosphate buffered saline with serum components, to provide a sample volume that is required by the particular immunoassay.

The term "specific binding member" refers to a member of a specific binding pair, i.e., two different molecules wherein one of the molecules through chemical or physical means specifically binds to the second molecule. In addition to antigen and antibody specific binding pairs such as the allergen and antibody pair, other specific binding pairs include biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for that sequence protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog. If the specific binding member is an immunoreactant it can be, for example, an antibody, antigen, hapten, or complex thereof. If an antibody is used, it can be a monoclonal or polyclonal antibody, a recombinant protein or antibody, a mixture or mixtures or a fragment or fragments thereof, as well as a mixture of an antibody and other specific binding members. The details of the preparation of such antibodies and their suitability for use as specific binding members are well-known to those skilled-in-the-art.

The term "indicator reagent" refers to an assay reagent comprising a detectable label directly or indirectly attached to a specific binding member which is capable of directly or indirectly binding to the analyte and thereby indicating the presence, absence or amount of the analyte in a test sample. A variety of different indicator reagents can be formed by varying either the label or the specific binding member. In general, the indicator reagent is detected after it has formed a complex with either the analyte or a complementary specific binding member, but the unbound indicator reagent can also be detected.

The term "label" refers to any substance which is attached to a specific binding member and which is capable of producing a signal that is detectable by visual or instrumental means. Labels can include chromogens; catalysts; fluorescent compounds; chemiluminescent compounds; radioactive isotopes; direct visual labels including colloidal metallic and non-metallic particles, dye particles, enzymes or substrates, or organic polymer latex particles; liposomes or other vesicles containing signal producing substances; and the like.

Many enzymes suitable for use as labels are disclosed in U.S. Pat. No. 4,275,149, columns 19–23, herein incorporated by reference. For example, an enzyme/substrate signal producing system useful with the substrate of the present invention is the enzyme alkaline phosphatase. If horse-radish peroxidase is used, o-Phenylenediamine is added as an enzyme substrate to form a colored product which can be detected and/or measured visually or instrumentally.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this system.

Another class of labels includes the visually detectable, colored particles which enable a direct colored readout of the presence or concentration of the analyte in the test sample without the need for using additional signal producing reagents. Materials for use as such particles include colloidal metals, such as gold, and dye particles as disclosed in U.S. Pat. Nos. 4,313,734 and 4,373,932. The preparation and use of non-metallic colloids, such as colloidal selenium particles, are disclosed in co-owned and copending U.S. patent application Ser. No. 072,084, filed Jul. 9, 1987, which is incorporated by reference herein. Organic polymer latex particles for use as labels are disclosed in co-owned and copending U.S. patent application Ser. No. 248,858, filed Sep. 23, 1988, which is incorporated by reference herein. The selection of a particular label is not critical, so long as the label is capable of generating a detectable signal either by itself or in conjunction with one or more additional signal producing substances.

The term "signal producing component" refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates to produce a detectable reaction product.

The term "capture binding member" refers to a specific binding member which can bind directly or indirectly to the analyte or indicator reagent and which is bound or is capable of being bound to a solid phase, or is capable of being precipitated, such that the capture binding member can be separated from the test sample and other assay reagents.

The term "capture reagent" refers to a capture binding member which is directly or indirectly attached to a solid phase material to enable the separation of the capture binding member, and analyte or indicator reagent that is bound thereto, from unbound analyte and assay reagents. Typically, the attachment of the capture binding member to the solid phase material is substantially irreversible and can include covalent mechanisms. The capture reagent of the present invention, however, is not limited to a capture binding member bound to an insoluble solid phase material. In an agglutination assay, the capture binding member of the capture reagent can be bound to a soluble carrier material such as bovine serum albumin.

In performing a capture reagent to be used in an assay, once the capture binding member, e.g., analyte specific antibody, is immobilized upon the solid phase, the remaining surface area of the solid phase is generally blocked with a suitable protein solution, such as bovine serum albumin, to prevent non-specific binding of protein to the support. The solid support is then washed with an appropriate solution to remove any excess blocking solution and/or unbound capture binding member.

Once complex formation occurs between the assay components, the solid phase can be used as a separation mechanism. For example, the reaction mixture can be contacted with the solid phase material, and the the solid phase material retains the newly formed reaction complex(es). Alternative methods can be used to perform this separation step, such as using a solid phase which itself binds to the capture binding member; affixing to the solid phase a binding member that is specific for the capture binding member; or affixing to the solid phase a reactive agent, such as a charged substance, which will attract and bind an oppositely charged substance that has been bound to the capture binding member, as disclosed in co-owned and copending U.S. patent application Ser. No. 150,278, filed Jan. 29, 1988, now abandoned which is incorporated by reference herein.

Assay devices can have many configurations, several of which are dependent upon the material chosen for the solid phase. The term "solid phase material" refers to any suitable chromatographic, bibulous, porous or capillary material or other conventional solid material, well-known to those skilled-in-the-art for use in immobilizing specific binding members. Solid phase materials can include a fiberglass, cellulose or nylon pad for use in a flow-through assay device having one or more layers containing one or more of the assay reagents; a dispstick for a dip and read assay; a test strip for chromatographic (e.g., paper or glass fiber) or thin layer chromatographic (e.g., nitrocellulose) techniques in which one or all of the reagents are contained in separate zones of a single strip of solid phase material; or an absorbent material well known to those skilled-in-the-art. The solid phase material can also include, without limitation, polyacrylamide beads, polystyrene beads or tubes, magnetic beads, a microtitre plate with one or more reaction wells or a glass or plastic test tube.

Natural, synthetic or naturally occurring materials that are synthetically modified, can be used as a solid phase material including polysaccharides, e.g., cellulose materials including paper, cellulose and cellulose derivatives such as cellulose acetate, nitrocellulose and cellulose acetate/nitrate; silica; fiberglass; inorganic materials such a deactivated alumina, diatomaceous earth or other inorganic finely divided material uniformly dispersed in a porous polymer matrix, with polymers such as vinyl chloride, vinyl chloride-propylene copolymer, and vinyl chloridevinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; agarose; Sephadex (Pharmacia Fine Chemicals, Inc., Piscataway, N.J.); Trisacryl (Pointet-Girard, France); silicon particles; porous fibrous matrixes; and the like. The solid phase material should have a reasonable inherent strength or strength can be provided by means of a support, and it should not interfere with the production of a detectable signal.

Optionally, the specific binding member of the capture reagent can be affixed to particles, e.g., microparticles. These microparticles can serve as the solid phase material and be retained in a column, suspended in a mixture of soluble reagents and test sample, or retained and immobilized by another solid phase base material. By "retained and immobilized" is meant that the microparticles, associated with the solid phase base material, are not capable of substantial movement to positions elsewhere within that material. The microparticles can be selected by one skilled-in-the-art from any suitable type of particulate material including those composed of polystyrene, polymethylcrylate, polypropylene, polytetrafluoroethylene, polyacrylonitrile, polycarbonate or similar materials. The size of the microparticles is not critical, although it is preferred that the average diameter be smaller than the average pore size of the solid phase base material if such is used.

The term "ancillary specific binding member" refers to a specific binding member used in addition to the capture binding member and the indicator reagent which becomes a part of the detectable binding complex. One or more ancillary specific binding members can be used in an assay. For example, an ancillary specific binding member can be used in an assay where the capture binding member is capable of binding the ancillary specific binding member which is in turn capable of binding the solid phase.

It will be appreciated by those skilled-in-the-art that the selection of any given label, ancillary binding member or solid phase material is generally not critical to the present invention. The materials are chosen to optimize the results provided by the chosen assay configuration. There are published reports that EDTA and EGTA inactivate alkaline phosphatase. For example, Pike, S. J. et al. report, *Biochem J* (England), Jun. 15, 1987, 244 (3), pages 781–785 a study of the inactivation of bovine intestinal mucosal alkaline phosphatase by EGTA, and Ackermann, B.P. et al. report, (*Biochem. J.* (1976) 153, 151–157, a study of the inactivation of pig kidney alkaline phosphatase by EDTA.

The use of 4-methylumbelliferyl phosphate as a substrate in carrying out immunoassays is also known. A capture reagent for the analyte, e.g., thyroid hormone, and alkaline phosphatase are first bound to a solid phase material, e.g., a nylon pad, and excess is then washed away; the sample is then brought into contact with the solid phase material and the capture reagent and alkaline phosphatase bound thereto, followed by another washing step; an antibody against the analyte brought into contact with the solid phase material, followed by still another washing step; 4-methylumbelliferyl phosphate substrate is then brought into contact with the solid phase material and the release of energy at a particular wavelength for a short period of time is measured. It has been found that the amount of energy released can be used to determine the amount of the analyte in the sample, but that alkaline phosphatase contamination of the substrate can make it inoperable.

BRIEF DESCRIPTION OF THE PRESENT INVENTION

The instant invention is based upon the discovery of a new 4-methylumbelliferyl phosphate substrate for use in immunoassays in which alkaline phosphatase is employed. Specifically, the new substrate contains from 0.01 to 0.05 gram moles per liter of EDTA or EGTA, and does not give false readings when there is an excess of alkaline phosphatase.

DESCRIPTION OF THE PREFERRED EMBODIMENTS

The invention will be more fully understood from the following examples, which constitute the best modes presently contemplated by the inventors. It is to be understood, however, that the examples are presented solely for the purpose of illustration, and are not to be construed as limiting.

As used herein, and in the appended claims, the terms "percent" and "parts" refer to percent and parts by weight, unless otherwise indicated; g means gram or grams; mg means milligram or milligrams; ng means nanogram or nanograms; cm means centimeter or centimeters; mm means millimeter or millimeters; L means liter or liters; μL means microliter or microliters; m/o means mole percent, and equals 100 times the number of moles of the constituent designated in a composition divided by the total number of moles in the composition; v/v means percent by volume; w/v means weight per unit of volume, and is in terms of g/L; M means molar and equals the number of gram moles of a solute in one liter of a solution; μM means micromolar and equals the number of microgram moles in one liter of a solution; N means normal, and equals the number of gram equivalents of a solute in one liter of solution; and μN means micronormal and equals the number of microgram equivalents of a solute in one liter of solution. All temperatures are in °C., unless otherwise indicated.

EXAMPLE 1

Under subdued light, a 1 L volumetric flask was charged with about 800 mL deionized water, and 0.1 gram mole of 2-amino-2-methyl-1-propanol. The contents of the flask were vortexed for about 30 minutes, and the solution in the flask was adjusted to a pH of 10.3 with 6N hydrochloric acid. A 0.01 gram mole portion of trisodium EDTA and a 1 g portion of sodium azide were then added to the flask, followed by vortexing for about 30 minutes. A 1.2 mg mole portion of 4-methylumbilliferyl phosphate and a 4 mg mole portion of tetramisole were then added to the solution in the flask, followed by vortexing until the last additions dissolved, and 6N aqueous sodium hydroxide was then added to adjust the pH of the solution to 10.3. Deionized water was then added to bring the total volume of the liquid in the flask to 1 L, and solids were separated from the solution which resulted by filtration. The filtrate was stored in a stoppered container in the dark for 48 hours before use.

The solution prepared as described in the preceding paragraph has been used to conduct IMx ® immunoassays of various analytes, and each of the analytes was subjected to the same assay using a conventional 4-methylumbelliferyl phosphate substrate which was identical to that prepared as described above except that the trisodium EDTA was omitted. The results of the assays with the substrate according to the invention correlated to 99+ percent with the results of the assays using the conventional substrate. The two 4-methylumbelliferyl phosphate substrates were also used to conduct immunoassays of calibrators of differing analyte concentrations for IMx ® assays for hTSH, FERRITIN, AFP, HCG and T3. The results, which are set forth in the following tables, indicated that the solution containing the EDTA was satisfactory for use as a substrate. In the tables, the data reported give the counts measured by the instrument. The first table gives the results with the substrate which contained EDTA while the second gives the results with the table which did not contain EDTA.

| Calibrator | IMx ® ASSAY hTSH | FERRITIN | AFP | HCG | T3 |
|---|---|---|---|---|---|
| A | 8.60 | 9.30 | 2.0 | 4.10 | 650.30 |
| B | 15.50 | 27.00 | 121.6 | 50.20 | 508.20 |
| C | 37.00 | 97.70 | 335.00 | 212.40 | 394.50 |
| D | 153.00 | 406.10 | 593.20 | 430.90 | 259.70 |
| E | 508.00 | 749.00 | 943.30 | 977.00 | 146.20 |
| F | 933.00 | 1212.20 | 1239.30 | 1586.50 | 74.70 |

| Calibrator | IMx ® ASSAY hTSH | FERRITIN | AFP | HCG | T3 |
|---|---|---|---|---|---|
| A | 8.00 | 5.70 | 3.00 | 3.00 | 686.00 |
| B | 14.60 | 25.00 | 105.30 | 34.10 | 550.00 |
| C | 32.50 | 103.10 | 293.60 | 146.90 | 461.00 |
| D | 137.50 | 443.50 | 502.00 | 293.50 | 313.00 |
| E | 448.80 | 785.50 | 777.30 | 696.30 | 180.00 |
| F | 962.90 | 1279.70 | 993.10 | 1188.80 | 105.00 |

It has been found that substrates are subject to contamination by alkaline phosphatase, and that the contamination can occur from human handling which occurs when the immunoassays are conducted, or when conjugates containing alkaline phosphatase are inadvertently introduced into the substrate, for example because they adhere to a pipette that is used in conducting IMx ® assays. It has also been found that the presence of alkaline phosphatase in substrates composed of 4-methylumbelliferyl phosphate solutions can destroy the ability of the solutions to perform as substrates. The conjugates used in all of the foregoing assays contain alkaline phosphatase, so there is a possibility of contamination with alkaline phosphatase of the substrates containing 4-methylumbilliferyl phosphate during the course of conducting the assays. The EDTA-containing and the conventional 4-methylumbelliferyl phosphate substrates produced as described above were tested by adding conjugate for the ferritin assay to each, and periodically pipetting 100 μL of each solution onto the matrix for the ferritin assay and taking a reading. After six days, the conventional 4-methylumbelliferyl phosphate substrate to which either 5 μL or 10 μL ferritin conjugate per 100 μL substrate had been added gave a reading above the maximum the available instrument can read, which means that the substrate was no longer operable to conduct the ferritin assay with that instrument. The substrate which contained EDTA, however, gave readings well below the maximum the instrument can read and, therefore, remained operable for use in the ferritin assay, for at least a month (the latest test time) after 5 μL and 10 μL additions of the ferritin conjugate were made thereto.

Substrates were also made by the procedure described above, except that different amounts of EDTA and various amounts of EGTA were used instead of the 0.01 gram mole portion of trisodium EDTA. The substrates produced contained 0.03 and 0.05 g mole per liter EDTA and 0.01, 0.03 and 0.05 g mole per liter EGTA. The substrates were found to be operable to perform the several IMx® immunoassays identified above, and to remain operable for extended periods of time after contamination with conjugates which contained alkaline phosphatase.

It will be appreciated from the foregoing discussion that the instant invention is a 4-methylumbelliferyl phosphate substrate for use in conducting an immunoassay which additionally contains from 0.01 to 0.05 gram mole per liter EDTA or EGTA. The presence of the EDTA or EGTA makes the substrate useful for extended periods of time, even after contamination with alkaline phosphatase. This is an unexpected result because it would have been anticipated that the EDTA or EGTA would attack binding sites for an enzyme and, therefore, make the 4-methylumbelliferyl phosphate solution inoperable as a substrate; instead, while there is slight interference, it is only necessary to increase the proportion of the 4-methylumbelliferyl phosphate in the substrate by to a small extent, e.g., by 10 to fifteen percent to overcome the interference. As disclosed above, the substrate contained 1.2 mg mole per L 4-methylumbelliferyl phosphate, which is considered optimum, although the concentration can range from 0.7 to 1.5 mg mole per liter 4-methylumbelliferyl phosphate. The substrate also contained 0.1 gram mole per L 2-amino-2-methyl-1-propanol and 4 mg moles tetramisole, which are desirably used for pH control, 1 g per liter sodium azide, which is also a desirable constituent, acting as a preservative. It is usually desirable for the substrate to be at a pH from about 10 to about 10.5. It is the presence of the EDTA or EGTA in the substrate that imparts resistance to deterioration when the substrate is contaminated with alkaline phosphatase, and this resistance is imparted to any 4-methylumbelliferyl phosphate substrate, regardless of pH and whether or not the other ingredients are present and regardless of the concentration of the 4-methylumbelliferyl phosphate in the substrate.

It will be apparent that various changes and modifications can be made from the specific details of the invention as described herein without departing from the spirit and scope thereof as defined in the following claims.

We claim:

1. Method of inhibiting the deterioration of a 4-methylumbelliferyl phosphate substrate solution by endogenous enzymes wherein said substrate is for use in conducting an immunoassay, said method comprises preparing a 4-methylumbelliferyl phosphate solution in an amount effective for use in conducting an immunoassay; and combining therewith from 0.01 to 0.05 gram mole per liter EDTA or EGTA wherein the pH of the resulting solution is from about 10 to about 10.5.

2. The method of claim 1 wherein from 0.01 to 0.05 gram mole per liter EDTA is combined with said substrate solution.

3. The method of claim 1 wherein from 0.01 to 0.05 gram mole per liter EGTA is combined with said substrate solution.

4. A method for producing a 4-methylumbelliferyl phosphate substrate for use in an immunoassay wherein said substrate can resist deterioration in the presence of endogenous enzyme during prolonged storage, said method comprising the addition of from 0.01 to 0.05 gram mole per liter EDTA or EGTA to a 4-methylumbelliferyl phosphate solution having a pH of from about 10 to about 10.5 suitable for use as a substrate in conducting an immunoassay.

5. A 4-methylumbelliferyl phosphate substrate for use in an immunoassay and resistant to deterioration by endogenous enzyme comprising 4-methylumbelliferyl phosphate and from 0.01 to 0.05 gram mole per liter EDTA or EGTA in a solution of pH from about 10 to about 10.5.

* * * * *